United States Patent
Ishida

(10) Patent No.: US 6,221,050 B1
(45) Date of Patent: Apr. 24, 2001

(54) SELF-RETAINING NEEDLE ASSEMBLY AND VALVE ELEMENT FOR USE THEREIN

(75) Inventor: Masahiro Ishida, Yamanashi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/416,523

(22) Filed: Oct. 12, 1999

(30) Foreign Application Priority Data

| Oct. 13, 1998 | (JP) | 10-290640 |
| Mar. 30, 1999 | (JP) | 11-088938 |
| Mar. 31, 1999 | (JP) | 11-092487 |

(51) Int. Cl.$^7$ ................................................. A61M 5/00
(52) U.S. Cl. ................................. 604/167.03; 604/256
(58) Field of Search .................. 137/843; 251/149.1; 604/256, 167.01–167.04, 164.04, 164.07

(56) References Cited

U.S. PATENT DOCUMENTS

| 4,929,235 | 5/1990 | Merry et al. ....................... 604/256 X |
| 5,389,080 | 2/1995 | Yoon ................................ 604/167.04 |
| 5,498,247 | 3/1996 | Brimball ........................... 604/256 X |
| 5,709,664 | 1/1998 | Vandenbroek et al. ........... 604/256 X |

FOREIGN PATENT DOCUMENTS

| 551017 | 7/1993 | (EP) . |
| 8-229133 | 9/1996 | (JP) . |
| 90/03822 | 4/1990 | (WO) . |

*Primary Examiner*—Anhtuan T. Nguyen
(74) *Attorney, Agent, or Firm*—Burns, Doane, Swecker & Mathis, LLP

(57) ABSTRACT

The invention provides a self-retaining needle assembly comprising a hollow outer needle, an outer needle hub that is provided at the basal end of said otter needle and which has a bore communicating with the interior of said outer needle, an inner needle to be passed through said outer needle, an inner needle hub provided at the basal end of said inner needle, and a valve element provided in the bore of said outer needle hub to plug said bore, characterized in that said valve element is a reversible valve element made of an elastic material that has a hole through which said inner needle can be passed. The assembly prevents the liquid leakage due to time-dependent deterioration and facilitates the injection of the blood and other fluids. The invention also provides a reversible element made of an elastic material that has a hole through which a tubular or rod member can be passed. The valve element also prevents the liquid leakage due to time-dependent deterioration.

27 Claims, 12 Drawing Sheets

SELF-RETAINING NEEDLE ASSEMBLY AND VALVE ELEMENT FOR USE THEREIN

BACKGROUND OF THE INVENTION

This invention relates to a self-retaining needle that is pierced into a blood vessel as in the case of transfusion. It also relates to a valve element for use in the needle.

To perform transfusion on a patient, a self-retaining needle to be connected to a transfusion line is pierced into a blood vessel of the patient and held in position. The self-retaining needle consists of a hollow outer needle, an outer needle hub secured to the basal end of the outer needle, an inner needle that is to be passed through the outer needle and which has a sharp tip point, and an inner needle hub secured to the basal end of the inner needle.

To pierce the self-retaining needle into a blood vessel of the patient, the inner needle is passed through the outer needle and pierced into the vessel as it projects from the tip of the outer needle. When the tip point of the inner needle gets into the blood vessel, the blood flows in through the opening in the tip and passes through the bore of the inner needle until it fills the interior of the transparent inner needle hub. This phenomenon is commonly called "flashback" and is a sign of the inner needle having secured the blood vessel. After the occurrence of "flashback", both the inner and outer needles are moved forward by a small distance until the tip of the outer needle enters the blood vessel. Then, with the outer needle being held between the finger and thumb, the inner needle is slipped out of the outer needle and the connector of a transfusion line is plugged to the outer needle hub.

The removal of the inner needle and connecting the transfusion line to the outer needle hub must be carried out as quickly as possible. If not, the blood flows back through the outer needle under the blood pressure and leaks out of the opening at the basal end of the outer needle hub to foul the surrounding area.

With a view to solving this problem, it was proposed that an elastic plug through which the inner needle could be pierced should be provided within the outer needle hub so that the liquid-tightness of the plug would prevent the blood from leaking out. An elastic plug assembly based on this idea is described in Unexamined Published Japanese Patent Application (kokai) No. 229133/1996.

The elastic plug assembly however has one major drawback. Before it is used, the inner needle remains pierced through the elastic plug but the portion of the plug which is in contact with the surface of the inner needle deteriorates over time and loses elasticity. If this occurs, the hole remaining after removing the inner needle is not fully closed and the blood may potentially leak out.

To deal with this problem, materials that will not deteriorate over time must be selected and used to make an effective elastic plug. However, the approach of preventing the time-dependent deterioration by selecting appropriate materials has inherent limits. In addition, desirable materials are very expensive and increase the production cost.

BRIEF SUMMARY OF THE INVENTION

The present invention has been accomplished under these circumstances and has as an object providing a self-retaining needle assembly that is free from liquid leakage due to deterioration with time.

Another object of the invention is to provide a valve element for use in the self-retaining needle assembly.

A further object of the invention is to provide a self-retaining needle assembly that allows the blood and other fluids to be injected easily.

These objects of the invention can be attained by the following.

(1) A self-retaining needle assembly comprising:
   a hollow outer needle;
   an outer needle hub that is provided at the basal end of said outer needle and which has a bore communicating with the interior of said outer needle;
   an inner needle to be passed through said outer needle;
   an inner needle hub provided at the basal end of said inner needle; and
   a valve element provided in the bore of said outer needle hub to plug said bore, wherein
   said valve element is a reversible valve element made of an elastic material that has a hole through which said inner needle can be passed.

(2) The self-retaining needle assembly as set forth in (1), wherein said valve element is funnel-shaped in at least the reversible portion thereof.

(3) The self-retaining needle assembly as set forth in (1) or (2), wherein said valve element has a cross section with a noncircular outer periphery before it is reversed and, when it is reversed, the sides that faced outward before the reversal come into close contact with each other.

(4) The self-retaining needle assembly as set forth in (3), wherein the cross section of said valve element before it is reversed has a polygonal outer periphery.

(5) The self-retaining needle assembly as set forth in (3), wherein the cross section of said valve element before it is reversed has an outer periphery consisting of arcs of a circle combined with straight lines.

(6) The self-retaining needle assembly as set forth in any one of (1)–(5), wherein the cross section of said valve element before it is reversed has an inner periphery that is identical or similar to the outer periphery of the cross section of said inner needle.

(7) The self-retaining needle assembly as set forth in any one of (1)–(6), wherein said valve element comprises thick-walled portions and thin-walled portions that extend along the periphery.

(8) The self-retaining needle assembly as set forth in any one of (1)–(7), wherein part or all of said valve element is made of a liquid-tight but gas-permeable material.

(9) The self-retaining needle assembly as set forth in any one of (1)–(8), wherein said valve element has soft portions that are made of a more flexible elastic material than the principal portion of said valve element and which come into contact with each other when said valve element is reversed.

(10) The self-retaining needle assembly as set forth in (9), wherein said soft portions contain an area that progressively decreases in thickness toward the distal end of said valve element.

(11) The self-retaining needle assembly as set forth in (9) or (10), wherein at least said soft portions of said valve element are made of a liquid-tight but gas-permeable material.

(12) The self-retaining needle assembly as set forth in any one of (9)–(11), wherein said soft portions have a rubber hardness (JIS TYPE A) of less than 95.

(13) The self-retaining needle assembly as set forth in any one of (1)–(12), wherein said inner needle is fitted with a reversal assisting means that assists in reversing said valve element.

(14) The self-retaining needle assembly as set forth in any one of (1)–(13), wherein said valve element is reversed with the aid of the friction that develops when said inner needle is pulled out of said hole.

(15) The self-retaining assembly as set forth in (13), wherein said valve element is reversed with aid of the action of said reversal assisting means when said inner needle is pulled out of said hole.

(16) A reversible valve element made of an elastic material that has a hole through which a tubular or rod member can be passed.

(17) The valve element as set forth in (16), which is funnel-shaped in at least the reversible portion thereof. (18) The valve element as set forth in (16) or (17), which has a cross section with a noncircular outer periphery before it is reversed and wherein, when it is reversed, the sides that faced outward before the reversal come into contact with each other.

(19) The valve element as set forth in (18), which has a cross section with a polygonal outer periphery before it is reversed.

(20) The valve element as set forth in (18), the cross section of which before it is reversed has an outer periphery consisting of arcs of a circle combined with straight lines.

(21) The valve element as set forth in any one of (16)–(20), which has a cross section with a generally circular inner periphery before it is reversed.

(22) The valve element as set forth in any one of (18) (21), which comprises thick-walled portions and thin-walled portions that extend along the periphery.

(23) The valve element as set forth in any one of (16)–(22), at least part of which is made of a liquid-tight but gas-permeable material.

(24) The valve element as set forth in any one of (16)–(23), which has soft portions that are made of a more flexible elastic material than the principal portion of said valve element and which come into contact with each other when said valve element is reversed.

(25) The valve element as set forth in (24), wherein said soft portions contain an area that progressively decreases in thickness toward the distal end of said valve element.

(26) The valve element as set forth in (24) or (25), wherein at least said soft portions are made of a liquid-tight but gas-permeable material.

(27) The valve element as set forth in any one of (24)–(26), wherein said soft portions have a rubber hardness (JIS TYPE A) of less than 95.

(28) The valve element as set forth in any one of (16)–(27), which is reversed with the aid of either the friction that develops when the tubular or rod member is pulled out of said valve element or a reversal assisting means that is provided on said tubular or rod member.

(29) The valve element as set forth in any one of (16)–(28), wherein said hole is formed in generally the center of said valve element.

DETAILED DESCRIPTION OF THE INVENTION

The self-retaining needle assembly and valve element of the present invention are described below in detail with reference to the preferred embodiments shown in the accompanying drawings.

Figure 1:
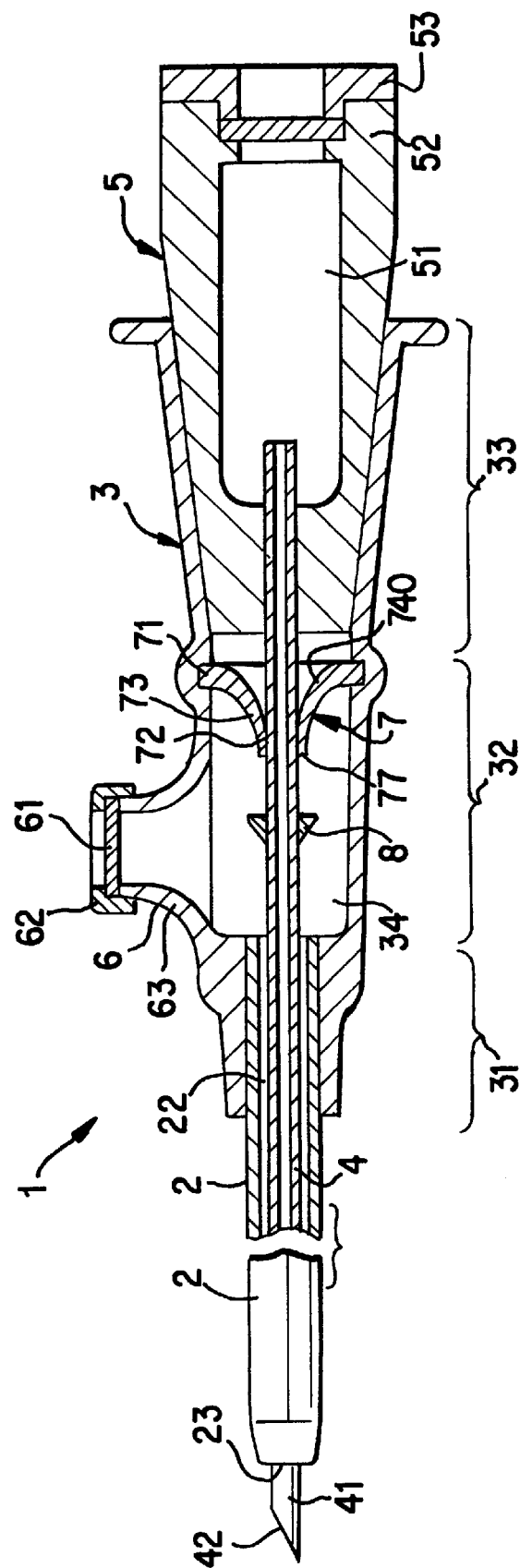
FIG. 1 is a longitudinal section of an example of the self-retaining needle assembly of the invention, with the inner and outer needles assembled.
Figure 2:
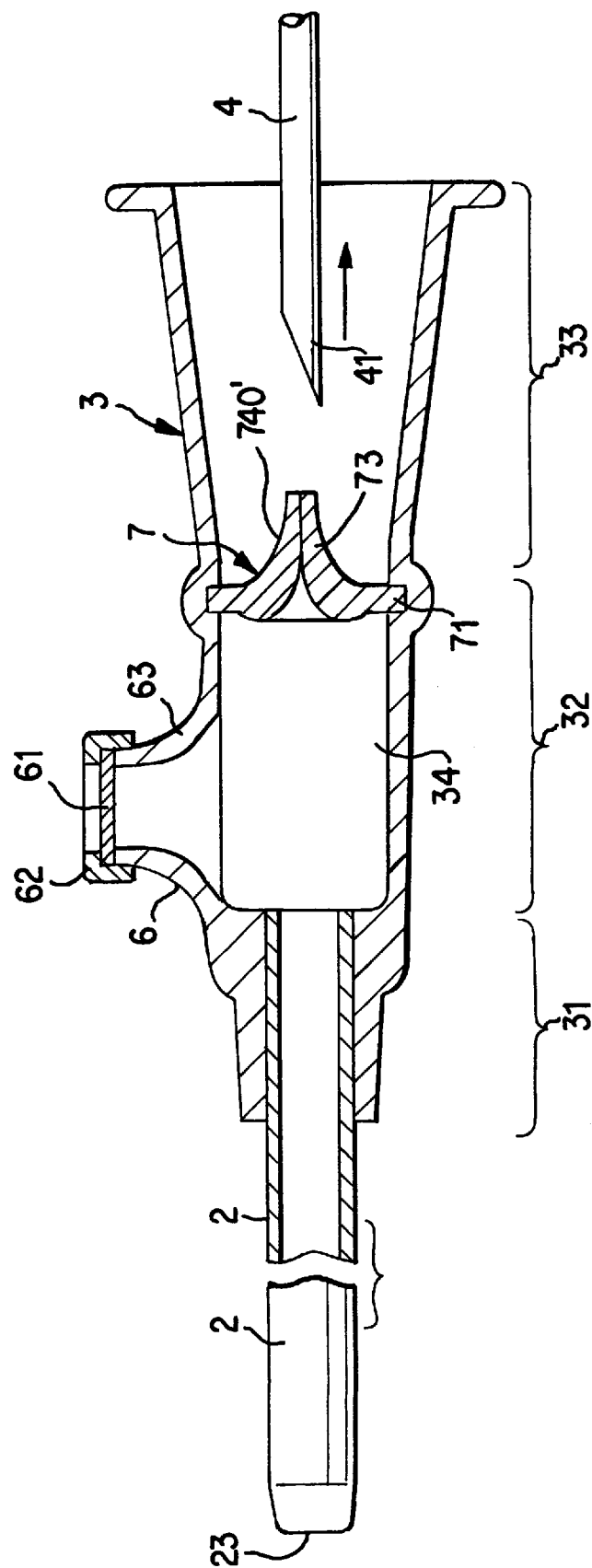
FIG. 2 is a longitudinal section of the self-retaining needle assembly, with the inner needle pulled from the outer needle.
Figure 3:
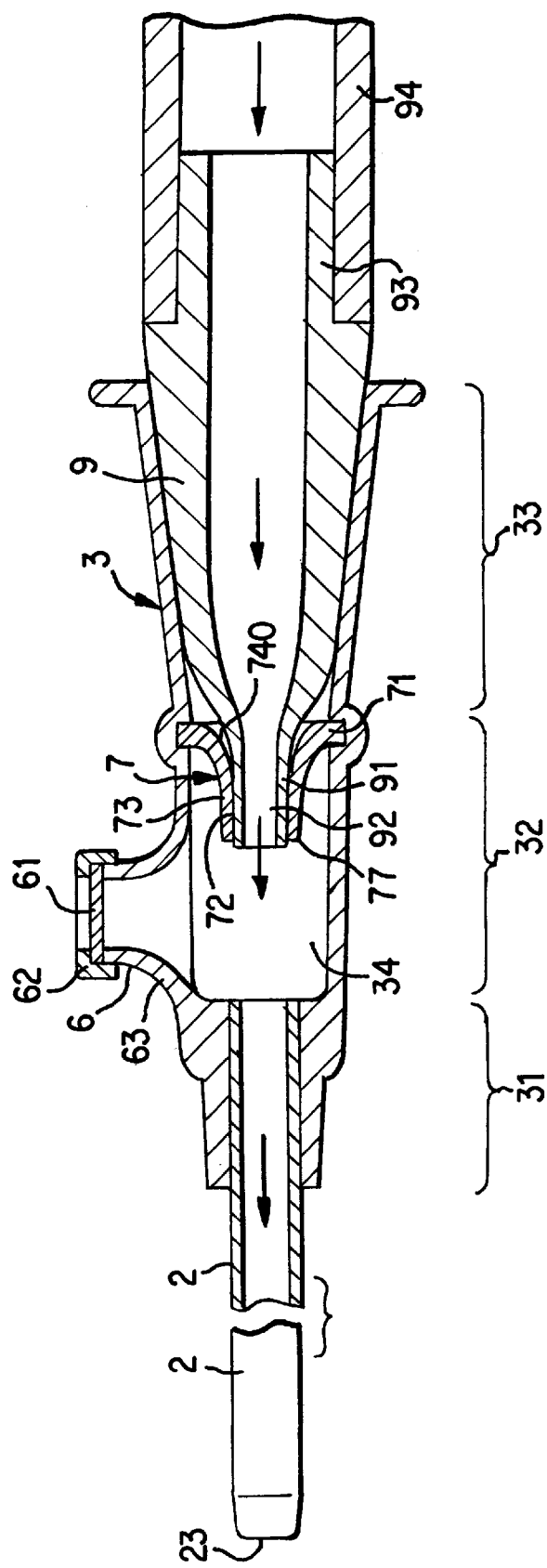
FIG. 3 is a longitudinal section of the self-retaining needle assembly, with a transfusing tool connected to the outer needle hub.
Figure 4:
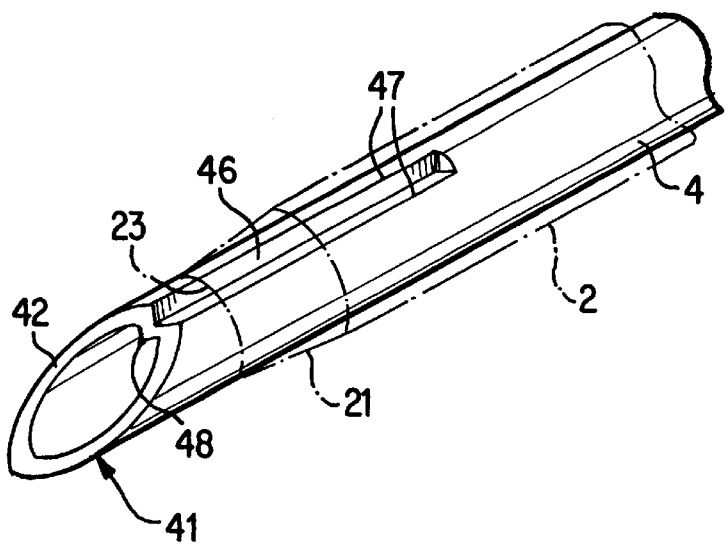
FIG. 4 is a perspective view of the distal end portion of the self-retaining needle assembly, with the inner and outer needles assembled.
Figure 5:
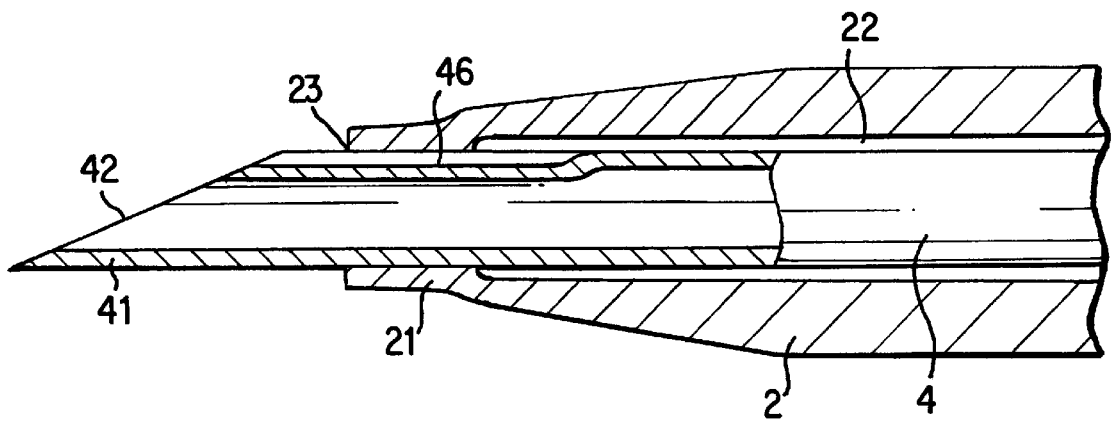
FIG. 5 is a longitudinal section of the distal end portion of the self-retaining needle assembly, with the inner and outer needles assembled.
Figure 6:
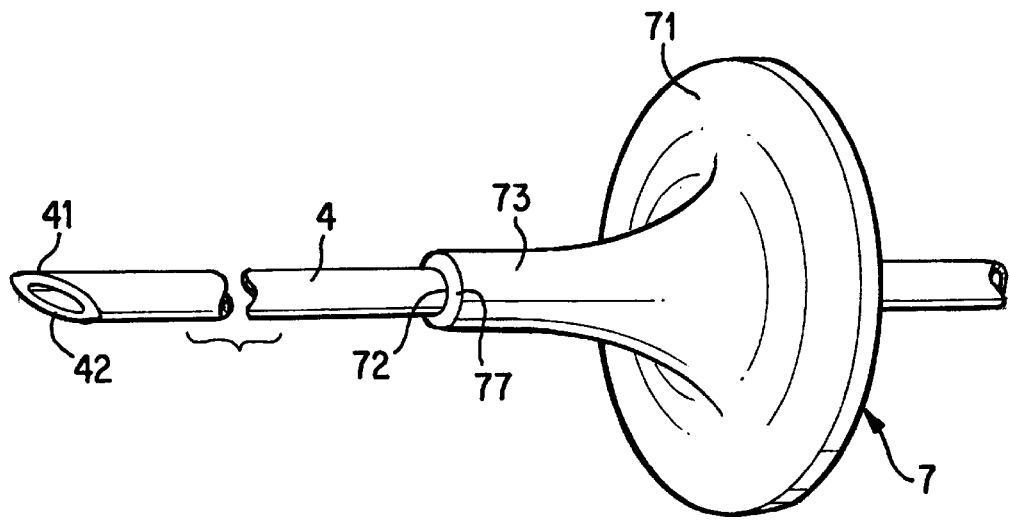
FIG. 6 is a perspective view of an example of the valve element of the invention before it is reversed.
Figure 7:
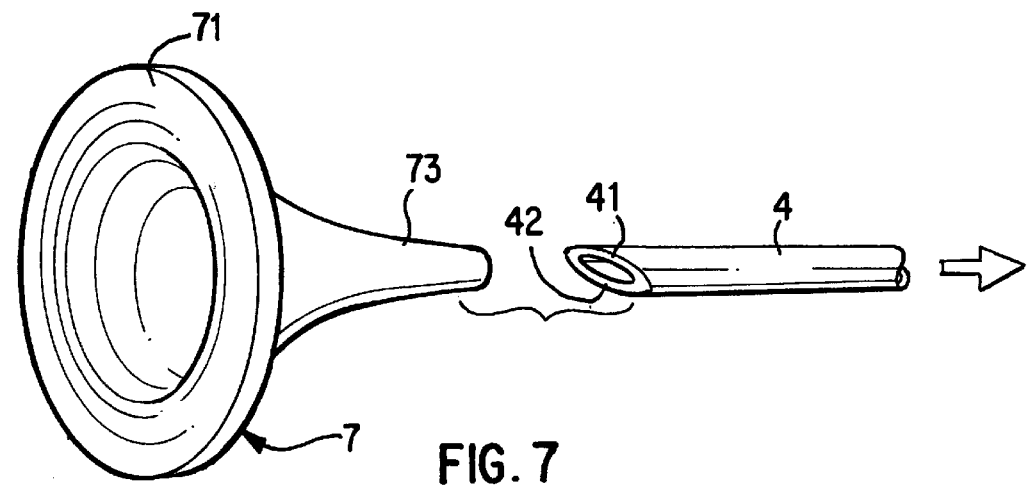
FIG. 7 is a perspective view of the valve element after it is reversed.

FIGS. 1, 2 and 3 are longitudinal sections showing an example of the self-retaining needle assembly of the invention. In FIG. 1, the inner and outer needles are shown assembled; in FIG. 2, the inner needle is shown to have been pulled out of the outer needle; in FIG. 3, a transfusion injecting tool is shown to have been connected to the outer needle hub. FIGS. 4 and 5 are a perspective view and a longitudinal view, respectively, of the distal end portion of the self-retaining needle assembly shown in FIGS. 1–3, with the inner and outer needles assembled. FIGS. 6 and 7 are perspective views showing the structure of the valve element of the invention. In the following description, the term "basal end" is used to designate the right side of FIGS. 1–7 and "distal end" is used to designate the left side.

As shown in FIGS. 1–5, the self-retaining needle assembly of the invention which is indicated by 1 comprises an outer needle 2 which is a self-retaining needle, an outer needle hub 3 provided at the basal end of the outer needle 2, an inner needle 4 to be passed through the outer needle 2, an inner needle hub 5 provided at the distal end of the inner needle 4, and a valve element (plug member) 7 provided within the outer needle hub 3. The individual components of the assembly are described below.

The outer needle 2 has the outer needle hub 3 secured liquid-tightly to the basal end. For details of the outer needle hub 3, see below. Suffice it here to say that the outer needle hub 3 is preferably made of a transparent (and colorless) resin, a colored transparent resin or a semitransparent resin to ensure that the bore 34 of the hub is visible.

In order to ensure that the outer needle 2 can be pierced into the human body easily and in a way that is not highly invasive, its tip is tapered, with the outside diameter decreasing progressively toward the distal end. A constricted portion 21 is formed at the farthest end of the outer needle 2. The inside diameter of the constricted portion 21 is set nearly equal to or slightly smaller than the outside diameter of the inner needle 4, so when the inner needle 4 is passed through the bore of the outer needle 2 until its tip point 41 projects beyond the opening 23 in the tip of the outer needle 2, the inner peripheral surface of the constricted portion 21 comes in close contact with the outer peripheral surface of the inner needle 4. Since this state is obtained when the inner needle hub 5 is fitted into the outer needle hub 3 as shown in FIG. 1, namely when the outer needle 2 and the inner needle 4 have been assembled (put together), it is hereunder referred to as an "assembled state".

The portion of the outer needle 2 that is the closer to the basal end than the constricted portion 21 has a larger outside diameter than the inner needle 4, so that in the assembled state, a predetermined clearance 22 is formed between the inner peripheral surface of the outer needle 2 and the outer peripheral surface of the inner needle 4. The clearance 22 provides a passageway for the blood.

The material of which the outer needle 2 is made is not limited in any particular way and various soft resins are preferably used, as exemplified by an ethylene-tetrafluoroethylene copolymer (ETFE), polyurethane and polyether nylon resin.

Preferably, part or all of the outer needle 2 is so adapted that its interior is visible. If desired, an X-ray contrast medium such as barium sulfate or barium carbonate may be incorporated in the constituent material of the outer needle 2 to allow its radiographic visualization.

The outer needle hub 3 is a substantially tubular member having an outer needle fixing portion 31 at the distal end that secures the outer needle 2 liquid-tightly; it also has a mating portion 33 (to be described later) at the basal end that mates with the inner needle hub 5 and a transfusion injecting tool 9. Formed between the outer needle fixing portion 31 and the mating portion 33 is an intermediate portion 32 that provides the bore 34 plugged with the valve member 7.

The method of fixing the outer needle 2 in the outer needle fixing portion 31 is in no way limited and may be exemplified by fusion (e.g., thermal fusion or rf fusion), bonding with an adhesive, fixing with a clamp or holding member (not shown) or combinations of these methods.

The mating portion 33 is a tapered tube that increases progressively in both inside and outside diameters toward the basal end so that it can mate with the inner needle hub 5 and the transfusion injecting tool 9 in an easy and positive way. In particular, the transfusion injecting tool 9 can be connected liquid-tightly. The surface of the mating portion 33 need not be smooth as shown in FIGS. 1–3 but may have a series of steps.

The intermediate portion 32 is in a cylindrical form having a substantially constant inside diameter. Its interior, or bore 34, communicates with the bore of the outer needle 2 which provides the clearance 22 when it is assembled with the outer needle 2.

An annular projection 6 is formed on the side of the intermediate portion 32 (which is shown in the top of FIGS. 1 and 2). The annular projection 6 provides an exhaust channel through which gases are discharged from within the bore 34 and it has a ventilation filter 61 at the end. The ventilation filter 61 is fixed with a ring of cap 62.

The ventilation filter 61 transmits gases but not liquids. Specific examples of the ventilation filter 61 include various porous sinters, hydrophobic non-woven cloths and other porous bodies. Preferred porous sinters are those prepared by sintering feeds containing both high-molecular weight materials (in powder) such as polyethylene and hydrophilic (water soluble and water swellable) polymers. When contacted by a liquid (blood), these porous sinters also prevent ventilation so there will be no ingress of air from the ambient atmosphere.

The annular projection 6 has a basal end 63 (remote from the ventilation filter 61) with a flared interior that communicates with the bore 34. This design has the advantage that irrespective of the position of the outer needle hub 3 (even if it is inclined from the horizontal), any gas bubbles within the bore 34 can float to be effectively discharged from it.

The exhaust channel is by no means limited to the annular projection 6 shown in FIGS. 1–3 and it may be a side hole formed through the wall of the outer needle hub 3. In this alternative case, the ventilation filter 61 is preferably provided in such a way that it closes the side hole.

The inner needle 4 is typically made of a metallic material selected from among stainless steel, aluminum, aluminum alloys, titanium, titanium alloys, and so forth. It has a sharp tip point 41, which is by no means limited in shape. In the example under consideration, the tip point 41 has a blade face 42 that forms a certain angle with the longitudinal axis of the inner needle 4.

The inner needle 4 has such a length that when it is assembled with the outer needle 2, at least the tip point 41 projects beyond the opening 23 in the tip of the outer needle 2 as shown in FIG. 1.

Preferably, the distal end portion of the inner needle 4 has a flute (cutout) 46 formed lengthwise in the outer periphery. The flute 46 provides a passageway for the blood. The area of the inner needle 4 where the flute 46 is formed lengthwise is that portion which at least makes close contact with the outer needle 2 when the two needles are assembled. Briefly, in the assembled state, the flute 46 is at least partly located in the area facing the constricted portion 21 of the outer needle 2 and it covers the axially extending area of the constricted portion 21. Specifically, the flute 46 is formed to run lengthwise from the base of the blade face 42 of the inner needle 4 over a distance that covers the axially extending area of the constricted portion 21.

With the flute 46 being thusly formed in the inner needle 4, a passageway for the blood is formed inside the constricted portion 21 of the outer needle 2 when it is assembled with the inner needle 4; this passageway allows the opening 23 in the tip of the outer needle 2 to communicate with the clearance 22 via the flute 46, thereby forming a continuous passageway for the blood.

The self-retaining needle is usually pierced into the human body with the blade 42 of the inner needle 4 facing up. Therefore, the flute 46 running lengthwise from the base of the blade face 42 offers the advantage that a flashback of the blood is readily visible as it passes through the constricted portion 21 (and, hence, the flute 46).

Both edges 47 of the flute 46 along which the flute 46 borders with the outer peripheral surface of the inner needle 4 are preferably round (formed to radius). If the edges 47 are sharp-angled, they may potentially damage the inner surface of the outer needle 2 as it receives the inner needle 4. There will be no such inconvenience if the edges 47 are round.

The method of forming the flute 46 is in no way limited and may be exemplified by grinding, laser processing and etching. In the example under consideration, the inner needle 4 is preferably formed by plastic deformation in plastic working, in particular, press working. This is because a flute 46 having round edges 47 and complexly shaped flutes that will be described later can be easily formed without finishing operations such as polishing and deburring.

Typically in the case of forming the flute 46 by press working, an inward projection 48 forms on the inner surface of the area of the inner needle 4 where the flute 46 is formed. In other words, the wall thickness of the inner needle 4 does not decrease significantly in the area where the flute 46 is formed but remains substantially constant in the entire periphery. This contributes to ensure that there will be no drop in the strength of the area of the inner needle 4 where the flute 46 is formed.

The shape and size of the flute 46 are not limited to any particular values as long as it is capable of covering the area of close contact between the inner needle 4 and the outer needle 2. In the illustrated case, the flute 46 preferably has a maximum depth of about 0.01–0.7 mm, more preferably about 0.05–0.45 mm; it preferably has a length of about 1–30 mm, more preferably about 1–15 mm. The width of the flute 46 is preferably about 0.1–1.5 mm, more preferably about 0.2–0.7 mm.

The cross-sectional shape, maximum depth, width and other geometric features of the flute 46 may remain constant or vary in the longitudinal direction of the inner needle 4. For example, the flute 46 may have a portion (particularly in the basal end portion) that progressively decreases (or increases) in maximum depth and/or width toward the basal end.

The flute 46 need not be straight as shown in FIG. 4. Alternatively, it may be curved as appropriate, formed in a serpentine path or made in a spiral form.

A plurality of flutes 46 may be formed in any positional relationship; for example, they may be arranged parallel to each other, at an angle with respect to a reference, or one flute may cross another. A single flute 46 may branch in a plurality of grooves part of the way.

The flute or flutes 46 provide passageways for the blood when the inner and outer needles are assembled. They may be replaced by any other structures that function as blood passageways; examples of such substitutes are chamfered cutouts and ground surfaces that are provided in the same area where the flute(s) 46 are formed.

As shown in FIG. 1, the inner needle 4 has the inner needle hub 5 secured liquid-tightly to the basal end. The internal space 51 of the inner needle hub 5 communicates with the bore of the inner needle 4. The inner needle hub 5 is preferably made of a transparent (and colorless) resin, a colored transparent resin or a semitransparent resin to ensure that the internal space 51 is visible.

To ensure that the inner needle hub 5 can be fitted into the mating portion of the outer needle hub 3, the tip of the inner needle hub 5 is tapered (reduced in outside diameter) toward the farthest end.

A ventilation filter 52 which is of the same type as the ventilation filter 61 is fitted at the basal end of the inner needle hub 5. This ventilation filter 52 is fixed with a ring of cap 53.

The outer needle hub 3 and the inner needle hub 5 may each be made of any suitable materials including, for example, polyolefins such as polyethylene, polypropylene and ethylene-vinyl acetate copolymers, poly(vinyl chloride), polyurethanes, polystyrenes, polycarbonates, polybutadienes, polyamides, polyesters such as poly(methyl methacrylate), poly(ethylene terephthalate) and poly(butylene terephthalate), as well as acrylic resins, ABS resins, ionomers, polyacetals, poly(phenylene sulfide) and polyetheretherketone.

A reversible valve element 7 that is capable of plugging the bore 34 of the outer needle hub 3 is provided within its intermediate portion 32 at the basal end. The shape, structure and other design features of the valve element 7 are described below.

As shown in FIGS. 1, 2, 6 and 7, the valve element 7 is formed of an elastic material and has a disk-shaped flange 71 in the outer periphery. The valve element 7 is installed and fixed by securing the entire periphery of the flange to the inner surface of the outer needle hub 3 by a suitable method such as fusion or bonding.

The valve element 7 has a deformable portion 73 that undergoes elastic deformation and which is formed inward of the flange 71 (and toward the distal end).

In the assembled state, the deformable portion 73 projects from the flange 71 toward the distal end of the valve element 7 such that it tapers toward its distal end. A hole 72 through which the inner needle 4 can pass is formed in the center of the deformable portion 73 (see FIG. 6). The overall shape of the valve element 7 may resemble a funnel as shown in FIG. 6. As is clear from FIGS. 1 and 6, with the inner needle 4 being passed through the hole 72, the deformable portion 73 has sufficient elasticity that the inner surface of the hole 72 makes intimate contact with the outer peripheral surface of the inner needle 4 to retain liquid-tightness.

The deformable portion 73 is a reversible portion that can be turned inside out. First assume that the inner needle 4 has been passed through the hole 72 (as shown in FIG. 6). As the inner needle 4 is pulled toward the basal end to be disengaged from the hole 72, the friction that develops between the inner surface 740 of the hole 72 and the outer peripheral surface of the inner needle 4 pulls the deformable portion 73 in the same direction so that the tip 77 of the deformable portion 73 gets into the hole 72 and moves progressively toward the basal end until the deformable portion 73 is completely reversed (as shown in FIG. 7).

Thus, the valve element 7 is reversed automatically as the inner needle 4 is pulled to be disengaged from the hole 72. Therefore, it can be easily reversed without any special techniques.

As is clear from FIGS. 2 and 7, the reversed deformable portion 73 projects toward the basal end. The surfaces of the deformable portion 73 that provided the outer periphery before the reversal now face inside (toward the center) and close the center hole since they closely contact each other under the elasticity of the deformable portion 73. As a result, the desired liquid-tightness is secured by the deformable portion 73 both before and after it is reversed.

Thus, in the assembled state with the inner needle 4 passed through the hole 72, the valve element 7 plugs the bore 34 liquid-tightly and prevents the blood from leaking out. Even after the inner needle 4 has been pulled out of the hole 72, the reversed deformable portion 73 effectively plugs the bore 34 liquid-tightly and prevents the blood from leaking out. If it becomes necessary to break the liquid-tight seal of the bore 34, as in the case of injecting transfusion, one may simply open the hole 72.

The valve element 7, particularly its deformable portion 73, may be made of any material that is selected from among various elastic (or soft) materials including, for example, natural rubber, synthetic rubbers such as isoprene rubber, silicone rubber, urethane rubber, styrene-butadiene rubber, fluorinated rubber and acrylic rubber, a porous body of polytetrafluoroethylene, polyamide-, polyester- and otherwise-based thermoplastic elastomers, and porous bodies of polyurethane.

The valve element 7 is preferably made of materials that are comparatively high in softness. The softness of elastic materials may typically be represented by the rubber hardness specified under JIS TYPE A. For the purposes of the present invention, at least the deformable portion 73 of the valve element 7 is preferably made of materials having a rubber hardness of less than 95, more preferably less than 65. Within this range, two important needs are satisfied, i.e., effective liquid-tightness is ensured both before and after reversal of the valve element 7, and ease (and positiveness) with which it can be reversed.

Preferably, part or all of the valve element 7, in particular, its deformable portion 73 is made of a liquid-tight but gas-permeable material. This offers the advantage that even if no exhaust channel of the type already described above is not provided, gases (e.g. their bubbles) within the bore 34 can be effectively discharged via the valve element 7. This property is possessed by various porous materials including porous bodies of polyurethane and polytetrafluoroethylene. Such porous materials may be rendered water-repellent before they are applied to make the valve element 7.

In the present invention, the deformable portion 73 of the valve element 7 is reversed to ensure that the liquid-tightness of the bore 34 is retained after the removal of the inner needle 4. Compared to the prior art, there is little or no need to take into account the time-dependent deterioration of the valve element 7 and this increases the latitude in selecting a suitable constituent material of the valve element 7. As a natural consequence, a broad range of materials including easily formable materials, mass-produced materials and inexpensive materials can be used to facilitate the manufacture of the valve element 7 at a lower cost.

The shape of the hole 72 is not limited to the illustrated circular type and it may assume any other shapes including an ellipse, and polygons such as octagon, hexagon, pentagon, rectangle and triangle. Alternatively, the hole 72 may be replaced by a single slit or a crossed slit.

As FIG. 1 shows, a ring of projection 8 as a means of assisting in the reversal of the valve element 7 is provided on the inner needle 4 in a position that is the closer to the distal end than the tip 77 of the valve element 7 in the assembled state. The projection 8 is fixed to the outer periphery of the inner needle 4 by a suitable method such as bonding with an adhesive or retaining as by clamping.

When the inner needle 4 is pulled toward the basal end, the projection 8 contacts the tip 77 of the deformable portion 73 and pushes it toward the basal end, thus permitting the deformable portion 73 to be reversed with greater ease.

The illustrated projection 8 is not the sole example of the reversal assisting means. If desired, the outer peripheral surface of the inner needle 4 may be roughened to increase its coefficient of friction.

Note that the reversal assisting means is optional and may be omitted if it is not necessary.

As FIG. 3 shows, the transfusion injecting tool 9 can be fitted liquid-tightly into the mating portion 33 of the outer needle hub 3. The transfusion injecting tool 9 used in the example under consideration is a connector fitted at the distal end of a transfusion line (transfusion feed line).

The transfusion injecting tool 9 has a constricted tip 91 which has a sufficient outside diameter to pass through the deformable portion 73 by pushing the hole 72 in the valve element 7 wide open. The tip 91 has an opening 92 in its interior.

The basal end 93 of the transfusion injecting tool 9 is connected to a flexible tube 94 which is a part of the transfusion line.

When the transfusion injecting tool 9 is advanced into the outer needle hub 3 until it engages and connects to the mating portion 33, its tip pushes the reversed deformable portion 73 toward the distal end so that the latter makes a second reversal to be reverted to the initial state. At the same time, the tip 91 of the blood injecting tool 9 pushes in to enlarge the hole 72 wide enough to permit its passage. As a result, the seal of the bore with the valve element 7 is broken and the interior of the blood injecting tool 9 communicates with the bore 34, allowing the blood or other fluids to be supplied from the injection tool 9 through the bore 34 into the ensuing bore in the outer needle 2.

The shape and structure of the blood injecting tool 9 are in no way limited to the illustrated case. It should particularly be noted that the tip 91 is by no means limited to a tubular type and may be replaced by any structure that is capable of forming a liquid passageway through the valve element 7. The blood injecting tool 9 to be connected to the outer needle hub 3 may be a syringe capable of injecting transfusion or drug solutions.

On the pages that follow, the shape the valve element 7 takes before it is reversed and the shape it takes after its reversal are described in greater detail.

Figure 8:
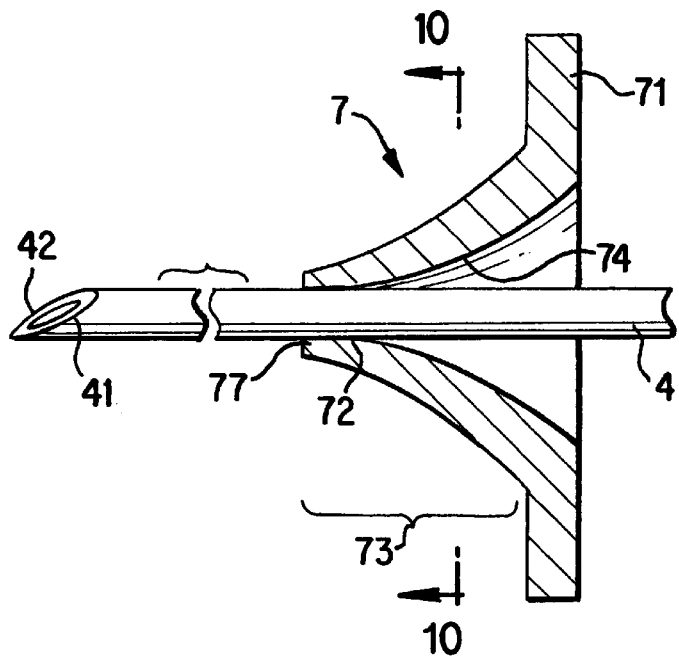
FIG. 8 is a longitudinal section of another example of the valve element of the invention before it is reversed.
Figure 9:
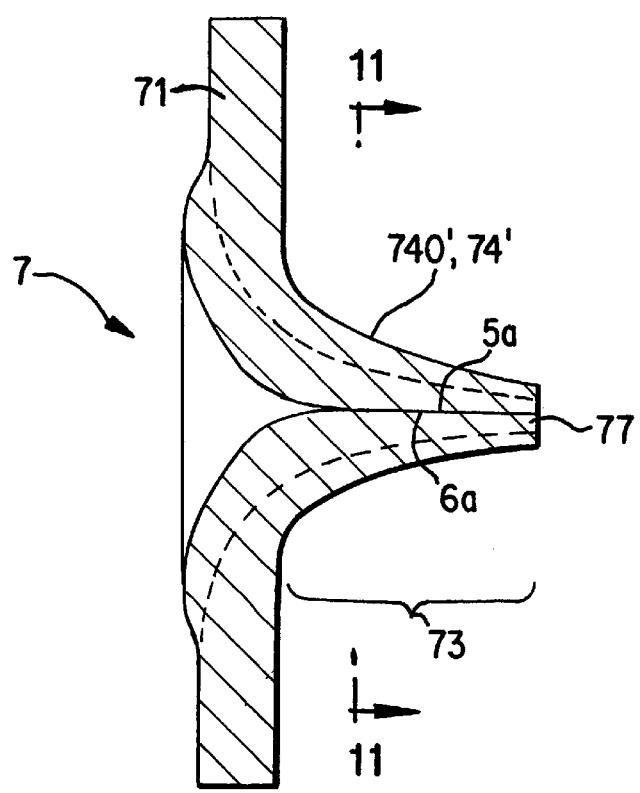
FIG. 9 is a longitudinal section of the valve element after it is reversed.
Figure 10:
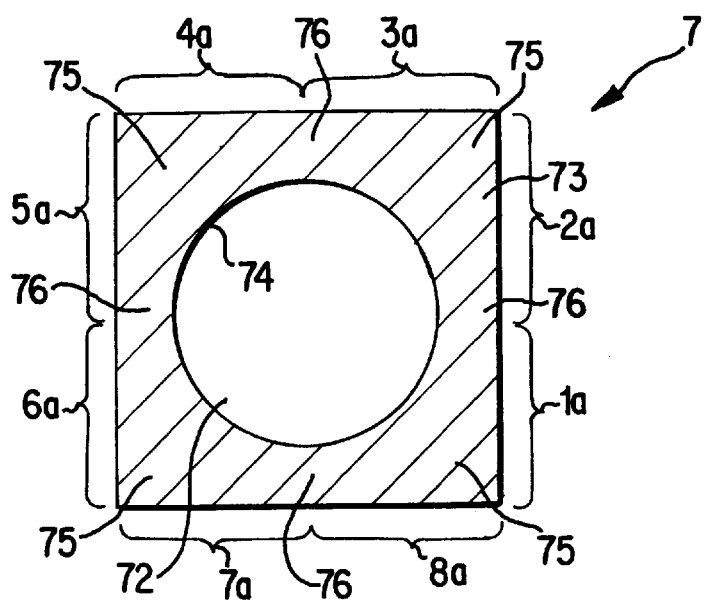
FIG. 10 is section A—A of FIG. 8.
Figure 11:
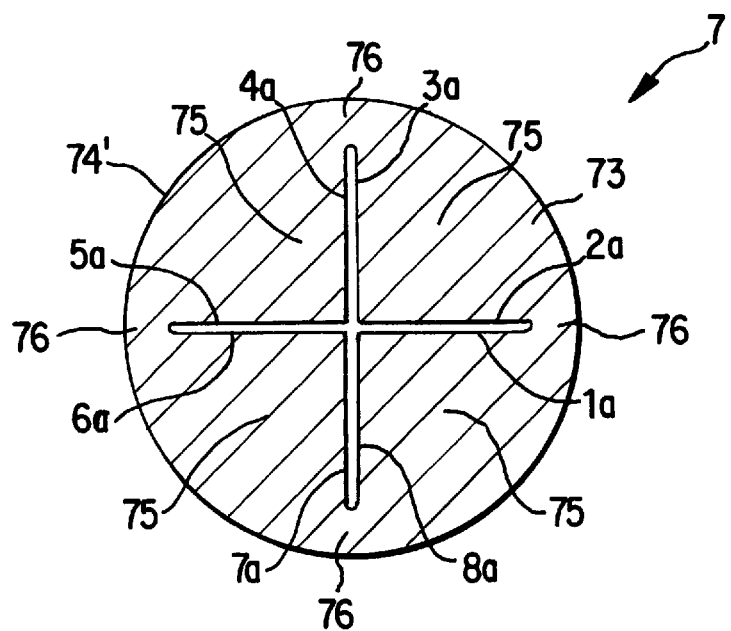
FIG. 11 is section B—B of FIG. 9.

FIGS. 8–11 show in section another example of the valve element of the invention. FIG. 8 is a longitudinal section of the deformable portion of the valve element 7 before it is reversed. FIG. 9 is a longitudinal section of the deformable portion after the valve element 7 was reversed. FIG. 10 is section A—A of FIG. 8, and FIG. 11 is section B—B of FIG. 9. The following description should be read with reference to these Figures.

It should be remembered that the valve element 7 shown in FIGS. 8–11 works in the same way to achieve the same advantages as described in connection with the example shown in FIGS. 1–7.

<1A> Shape of the valve element before it is reversed (see FIGS. 8 and 10)

Before reversal of the valve element 7, the inner surface 74 of the deformable portion 73 has a cross section with an inner peripheral shape that is either identical or similar to the cross-sectional shape of the outer periphery of the inner needle 4, which is circular as shown in FIG. 10. Because of this shape, the valve element 7 makes a close enough contact with the outer peripheral surface of the inner needle 4 to secure the desired liquid-tightness.

Before reversal of the valve element 7, the outer surface of the deformable portion 73 has a cross section with a noncircular peripheral shape. As shown in FIG. 10, the cross section of the deformable portion 73 has a square outer peripheral shape.

The deformable portion 73 of the valve element 7 has a thick-walled area 75 and a thin-walled area 76 that alternate in a peripheral direction. Specifically, the thick-walled area 75 is formed near the four corners of the square, with the thin-walled area 76 lying near the center of each side of the square.

For the sake of convenience in describing the shape of the valve element 7 after it is reversed, let us divide the outer peripheral surface of the deformable portion 73 into eight equal areas in the peripheral direction and call them flat planes 1a–8a.

<2A> Shape of the valve element after its reversal (see FIGS. 9 and 11)

When the valve element 7 is reversed, it is turned inside out and the inner surface 74 before the reversal comes outside whereas the outer surface (planes 1a–8a) comes inside. Briefly, the outer surface 74' of the reversed deformable portion 73 was the inner surface 74 before the reversal, except that it has been expanded. As shown in FIG. 11, the surface 74' has a circular cross section.

The planes 1a–8a which composed the outer peripheral surface of the deformable portion 73 before the reversal are tucked in to contact each other. Specifically, after the reversal, plane 1a comes into contact with plane 2a, plane 3a with plane 4a, plane 5a with plane 6a, and plane 7a with plane 8a, whereby the inside of the deformable portion 73 is sealed liquid-tightly. In other words, the four thick-walled areas 75 including the four corners press against each other on their outer surfaces crossing at right angles, thereby providing liquid-tight seal inside the deformable portion 73.

In FIG. 11, the mating surfaces identified above are shown to be spaced apart to form a generally cross-shaped gap but this is for providing clarity to the relative positions of the individual planes 1a–8a and, in fact, the mating surfaces are in close contact with each other to leave no such gap.

As described above, the valve element 7 secures liquid-tightness not only before it is reversed; even after it is reversed, the planes 1a–8a which composed the outer surface before the reversal come into close contact with each other to seal the inside of the deformable portion 73, thereby securing liquid-tightness. Thus, in the assembled state (with the inner needle 4 passed through the hole 72), the valve element 7 seals the bore 34 liquid-tightly to prevent the blood from leaking out; even after the inner needle 4 is pulled out of the hole 72, the surfaces of the reversed deformable portion 73 come into close contact with each other to provide liquid-tight seal, thereby preventing the blood from leaking out. If it becomes necessary to break the liquid-tight seal of the bore 34 as in the case of injecting transfusion, one may simply open the hole 72.

In the embodiment under consideration, the cross section of the deformable portion 73 to be reversed has a noncircular (specifically, square) outer periphery and, when the valve element 7 is reversed, the respective parts of the deformable portion 73 (in particular, the thick-walled area 75 and the thin-walled area 76) are turned inside out in specified directions to ensure that they are reversed in an ordered manner. As a result, the valve element 7 can be reversed easily and positively.

Referring to the thick-walled area 75 and the thin-walled area 76, the latter has the smaller elastic modulus. Therefore, as the inner needle 4 is moved toward the basal end to be pulled out of the hole 72, the deformable portion 73 behaves as follows when the deformable portion 73 is pulled toward the basal end by the friction that develops between the inner surface 74 of the valve element 7 and the outer peripheral surface of the inner needle 4; the more easily deformable thin-walled areas 76 first get into the hole 72 to become inside out and subsequently the thick-walled areas 75 are turned inside out. Thus, the valve element 7 has a thickness distribution in the peripheral direction and the thin-walled areas 76 with the smaller elastic modulus provide the start point of the reversal of the deformable portion 73; as the thin-walled areas 76 are reversed, the remaining areas of the deformable portion 73 are also reversed as if they were "pulled" by the thin-walled areas 76. In this way, the deformable portion 73 can be reversed easily and positively.

It should be particularly noted that even if the area near the inner surface 74 of the deformable portion 73 deteriorates with time to reduce the adhesion (friction) between said inner surface 74 and the outer peripheral surface of the inner needle 4, the valve element 7 retains the advantage of being reversed easily and positively. This advantage is hereunder described as the "ease and positiveness in the reversal of the valve element 7".

Figure 12:
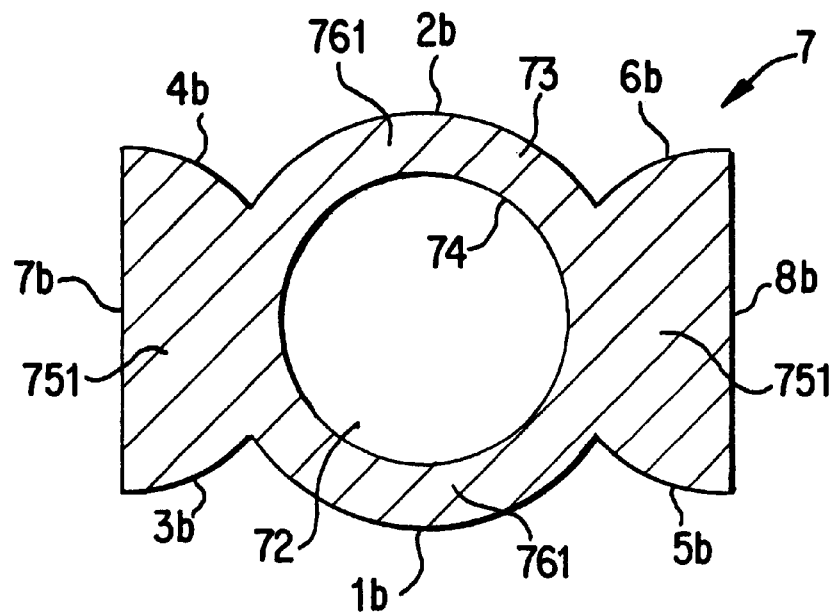
FIG. 12 is a cross section of yet another example of the valve element of the invention before it is reversed.
Figure 13:
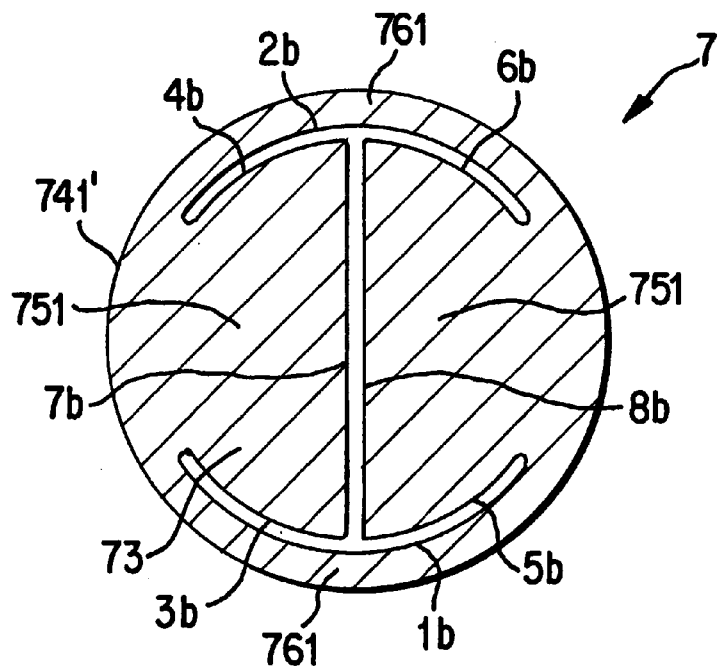
FIG. 13 is a cross section of the valve element after it is reversed.

FIGS. 12 and 13 show in section yet another example of the valve element of the invention. FIG. 12 is a cross section of the deformable portion of the valve element 7 before it is reversed. FIG. 13 is a cross section of the deformable portion after the valve element 7 was reversed. The shapes of the valve element 7 it assumes before and after it is reversed are described below with reference to these Figures.

<1B> Shape of the valve element before it is reversed (see FIG. 12).

Before reversal of the valve element 7, the inner surface 741 of the deformable portion 73 has a cross section with an inner peripheral shape that is either identical or similar to the cross-sectional shape of the outer periphery of the inner needle 4, which is circular as shown in FIG. 12. Because of this shape, the valve element 7 makes a close enough contact with the outer peripheral surface of the inner needle 4 to secure the desired liquid-tightness.

Before reversal of the valve element 7, the outer surface of the deformable portion 73 has a cross section with a noncircular peripheral shape. As shown in FIG. 12, the cross section of the deformable portion 73 has a so-called "candy" shape, which consists of a pair of opposed arcs of a circle (arcuate curved surfaces) 1b and 2b, arcs of a circle (arcuate curved surfaces) 3b, 4b, 5b and 6b that are connected to opposite ends of the arcs 1b and 2b and which are about one half of their length, a straight line (flat plane) 7b that connect the opposite ends of the arcs 3b and 4b, and a straight line (flat plane) 8b that connects the opposite ends of the arcs 5b and 6b.

The deformable portion 73 of the valve element 7 has a thick-walled area 751 and a thin-walled area 761 that alternate in a peripheral direction. Briefly, the thick-walled area 751 is formed between the inner surface 741 and each of the straight lines (flat planes) 7b and 8b, whereas the thin-walled area 761 is formed between the inner surface 741 and each of the arcs (curved surfaces) 1b and 2b.

<2B> Shape of the valve element after its reversal (see FIG. 13)

When the valve element 7 is reversed, it is turned inside out and the inner surface 741 before the reversal comes out whereas the outer surface (planes 1b–8b) comes inside. Briefly, the outer surface 741' of the reversed deformable portion 73 was the inner surface 741 before the reversal, except that it has been expanded. As shown in FIG. 13, the surface 741' has a circular cross section.

The planes 1b–8b which composed the outer peripheral surface of the deformable portion 73 before the reversal are tucked in to contact each other. Specifically, after the reversal, plane 1b comes into contact with planes 3b and 5b, plane 2b with planes 4b and 6b, and plane 7b with plane 8b, whereby the inside of the deformable portion 73 is sealed liquid-tightly. In other words, the two thick-walled areas 751 press against each other on their surfaces 7b and 8b, thereby providing liquid-tight seal inside the deformable portion 73.

In FIG. 13, the mating surfaces identified above are shown to be spaced apart to form a generally H-shaped gap but this is for providing clarity to the relative positions of the individual planes 1b–8b and, in fact, the mating surfaces are in close contact with each other to leave no such gap.

The valve element 7 shown in FIGS. 12 and 13 has the same advantage as described in connection with the embodiment shown in FIGS. 1–7 and, in particular, it provides the same ease and positiveness in reversal as have been described in connection with the embodiment shown in FIGS. 8–11.

Figure 14:
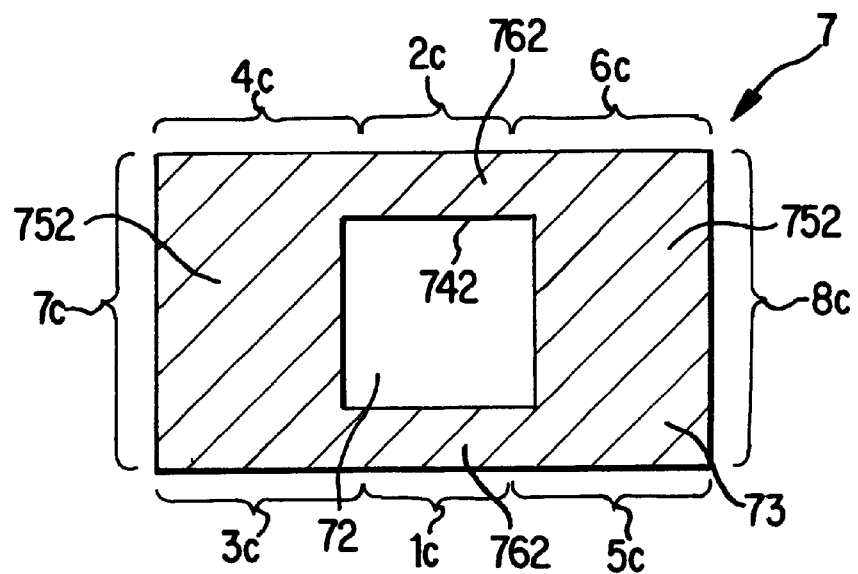
FIG. 14 is a cross section of still another example of the valve element of the invention before it is reversed.
Figure 15:
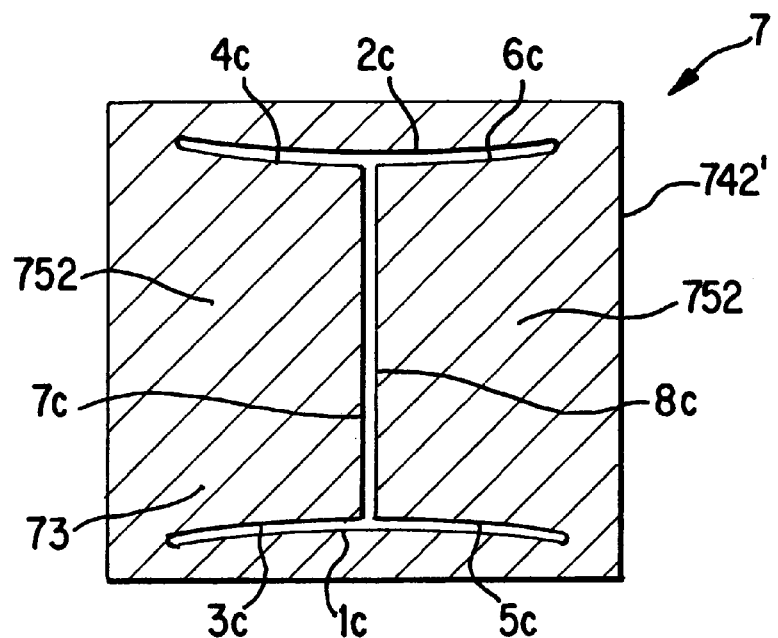
FIG. 15 is a cross section of the valve element after it is reversed.

FIGS. 14 and 15 show in section still another example of the valve element of the invention. FIG. 14 is a cross section of the deformable portion of the valve element 7 before it is reversed. FIG. 15 is a cross section of the deformable portion after the valve element 7 was reversed. The shapes of the valve element 7 it assumes before and after it is reversed are described below with reference to these Figures.

<1C> Shape of the valve element before it is reversed (see FIG. 14)

Before reversal of the valve element 7, the inner surface 742 of the deformable portion 73 has a cross section with a square inner peripheral shape, as shown in FIG. 14. The valve element 7 shown in FIG. 14 is suitable for use with either an inner needle 4 of a rectangular, especially square, cross-sectional shape or otherwise shaped rods. If used with such inner needle 4 and rods, the valve element 7 contacts their outer surfaces so closely that it secures outstanding liquid-tightness.

Before reversal of the valve element 7, the outer surface of the deformable portion 73 has a cross section with a noncircular outer peripheral shape. As shown in FIG. 14, the cross section of the deformable portion 73 has a rectangular outer peripheral shape "candy" shape. The outer surface of the deformable portion 73 consists of flat planes 1c–8c.

The deformable portion 73 of the valve element 7 has a thick-walled area 752 and a thin-walled area 762 that alternate in a peripheral direction. Briefly, the thick-walled area 752 is formed between the inner surface 742 and each of the planes 7c and 8c, whereas the thin-walled area 762 is formed between the inner surface 742 and each of the planes 1c and 2c.

<2C> Shape of the valve element after its reversal (see FIG. 15)

When the valve element 7 is reversed, it is turned inside out and the inner surface 742 before the reversal comes outside whereas the outer surface (planes 1c–8c) comes inside. Briefly, the outer surface 742' of the reversed deformable portion 73 was the inner surface 742 before the reversal, except that it has been expanded. As shown in FIG. 15, the surface 742' has a generally square (or rectangular) cross section.

The planes 1c–8c which composed the outer peripheral surface of the deformable portion 73 before the reversal are tucked in to contact each other. Specifically, after the reversal, plane 1c comes into contact with planes 3c and 5c, plane 2c with planes 4c and 6c, and plane 7c with plane 8c, whereby the inside of the deformable portion 73 is sealed liquid-tightly. In other words, the two thick-walled areas 752 press against each other on their surfaces 7c and 8c, thereby providing liquid-tight seal inside the deformable portion 73.

In FIG. 15, the mating surfaces identified above are shown to be spaced apart to form a generally H-shaped gap but this is for providing clarity to the relative positions of the individual planes 1c–8c and, in fact, the mating surfaces are in close contact with each other to leave no such gap.

The valve element 7 shown in FIGS. 14 and 15 has the same advantage as described in connection with the embodiment shown in FIGS. 1–7 and, in particular, it provides the same ease and positiveness in reversal as have been described in connection with the embodiment shown in FIGS. 8–11.

Figure 16:
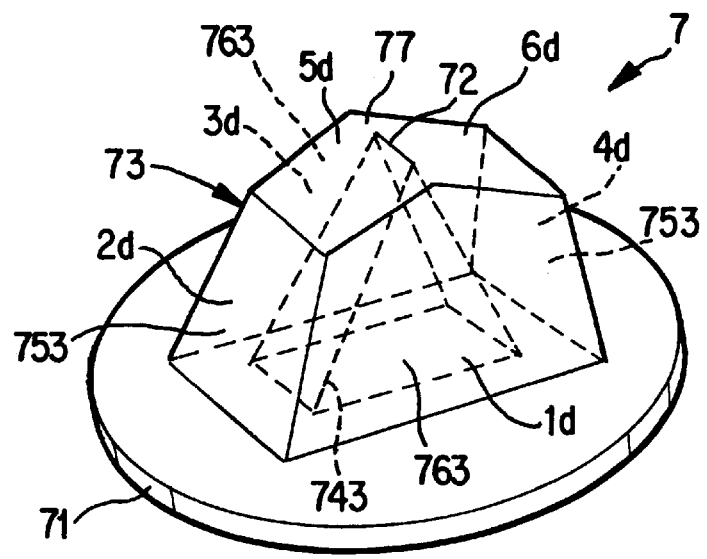
FIG. 16 is a perspective view of a further example of the valve element of the invention before it is reversed.
Figure 17:
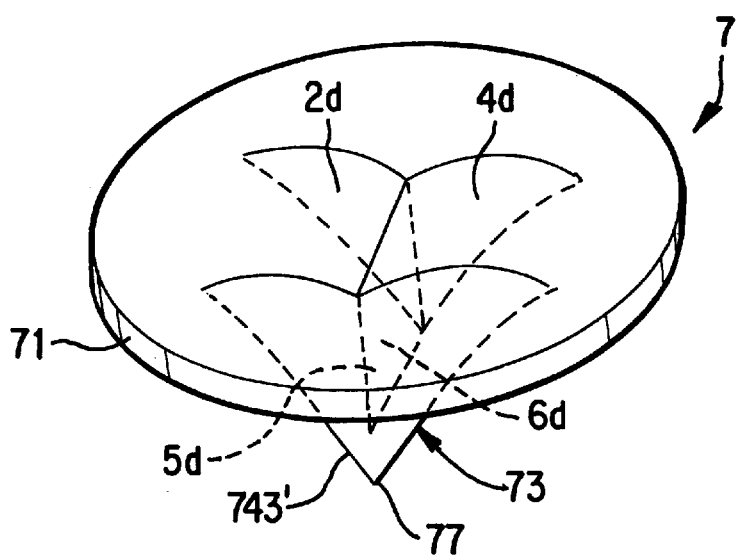
FIG. 17 is a perspective view of the valve element after it is reversed.
Figure 18:
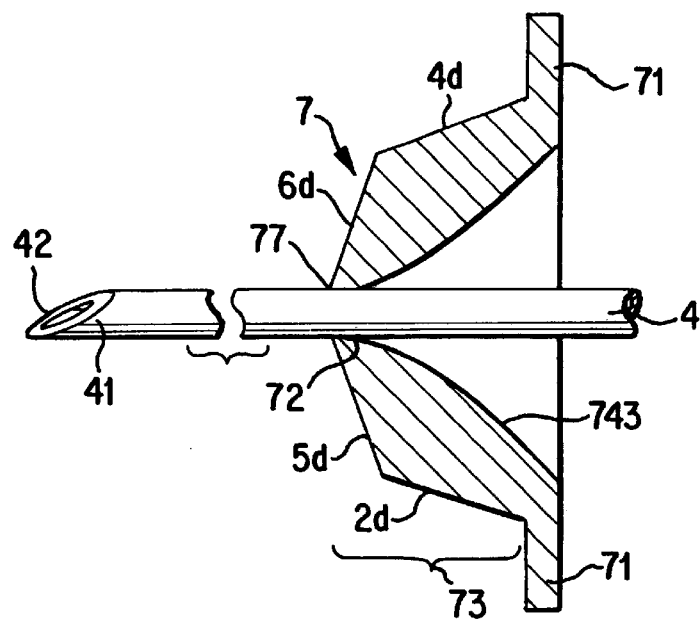
FIG. 18 is a longitudinal section of another example of the valve element of the invention before it is reversed.
Figure 19:
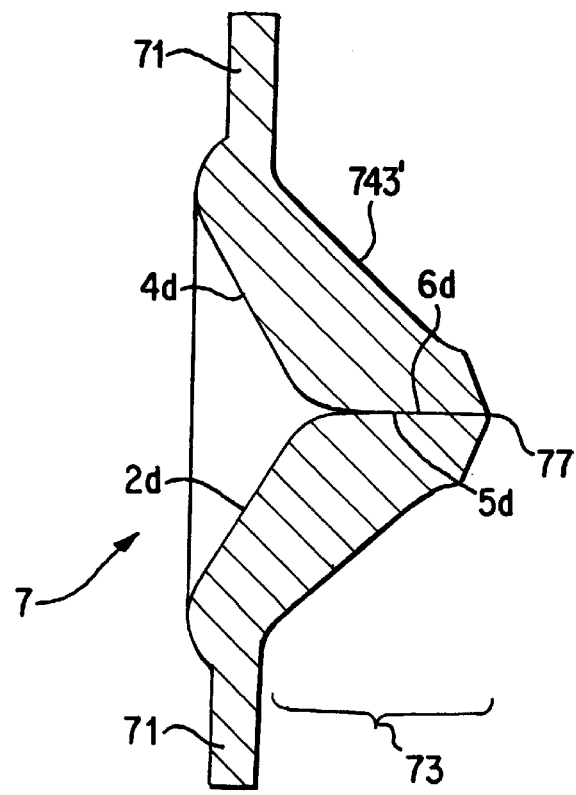
FIG. 19 is a longitudinal section of the valve element after it is reversed.

FIGS. 16–19 show in perspective or section another example of the valve element of the invention. FIG. 16 is a perspective view of the deformable portion of the valve element 7 before it is reversed. FIG. 17 is a perspective view of the deformable portion after the valve element 7 was reversed. FIGS. 18 and 19 are longitudinal sections of the valve element shown in FIGS. 16 and 17, respectively. The shapes of the valve element 7 it assumes before and after it is reversed are described below with reference to these Figures.

<1D> Shape of the valve element before it is reversed (see FIGS. 16 and 18)

As typically shown in FIG. 16, the overall shape of the deformable portion 73 it assumes before the valve element 7 is reversed has a cross section generally consisting of a trapezoid with a triangle on its top. Specifically, the outer surface of the deformable portion 73 consists of four sides 1d–4d on the outer periphery and two vertices 5d and 6d on the top.

Before the reversal of the valve element 7, the inner surface 743 of the deformable portion has a cross section with an inner periphery which is rectangular as indicated by the dashed line in FIG. 16.

Before reversal of the valve element 7, the outer surface of the deformable portion 73 which consists of planes 1d–4d has a cross section with a noncircular outer peripheral shape. As shown in FIG. 16, the cross section of the deformable portion 73 has a rectangular outer peripheral shape.

The deformable portion 73 of the valve element 7 has a thick-walled area 753 and a thin-walled area 763 that alternate in a peripheral direction. Briefly, the thin-walled area 763 is formed near the outer peripheral surfaces 1d and 3d, whereas the thick-walled area 753 is formed near the outer peripheral surfaces 2d and 4d.

<2D> Shape of the valve element after its reversal (see FIGS. 17 and 19)

The reversing angle of the valve element 7 (the change in angle relative to the deformable portion 73) is typically about 90 degrees. When the valve element 7 is reversed, it is turned inside out and the inner surface 743 before the reversal comes outside whereas the outer peripheral surface (planes 1d–4d) and vertices 5d and 6d come inside. Briefly, the outer surface 743' of the reversed deformable portion 73 was the inner surface 743 before the reversal, except that it has been expanded. The outer surface 743' has a rectangular cross section.

The vertices 5d and 6d which were part of the outer surface of the deformable portion 73 before the reversal are tucked in to contact each other. Briefly, after the reversal, vertex 5d comes into contact with the vertex 6d so that the inside of the deformable portion 73 is sealed liquid-tightly.

The valve element 7 shown in FIGS. 16–19 has the same advantage as described in connection with the embodiment shown in FIGS. 1–7 and, in particular, it provides the same ease and positiveness in reversal as have been described in connection with the embodiment shown in FIGS. 8–11.

The valve elements of the embodiments described on the foregoing pages are shown to be made of one kind of elastic material but this is not the sole case of the invention and the valve element 7 may be formed of two or more materials in combination that have different compositions or characteristics.

For example, the valve element 7 may be a laminate of two or more layers. Specifically, two layers made of different materials are superposed to provide opposite faces of the valve element 7 with desired settings of various conditions including friction, elasticity (expanding and shrinking properties) and adhesion (liquid-tightness).

Stated more specifically, the valve element 7 may consist of two or more materials having different degrees of elasticity or softness (rubber hardness) that are either joined or integrated together. If the valve element 7 is so constructed that the more flexible areas are brought into close contact with each other after it is reversed, an even higher level of liquid-tightness can be provided by the reversed valve element. If desired, the valve element 7 may be made of two or more materials having different degrees of air permeability or surface frictional resistance that are joined or integrated together.

Figure 20:
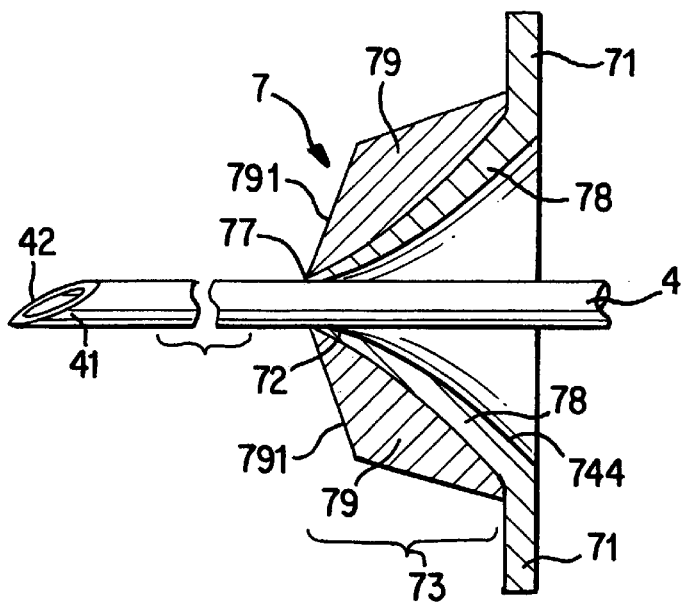
FIG. 20 is a longitudinal section of yet another example of the valve element of the invention before it is reversed.
Figure 21:
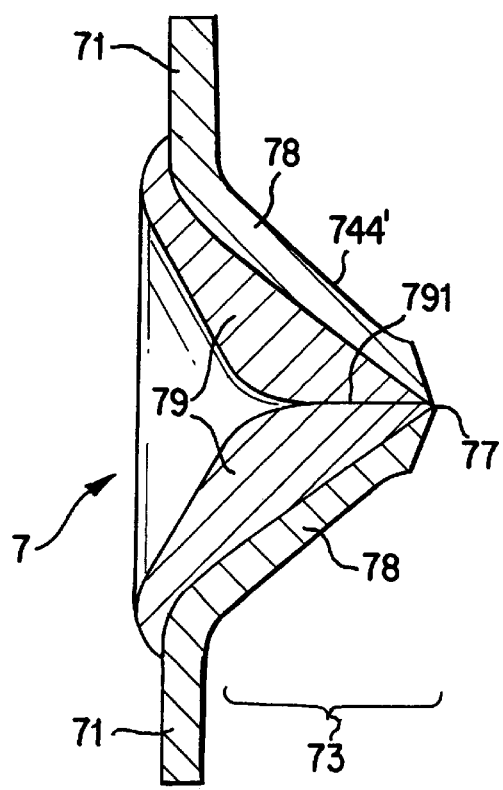
FIG. 21 is a longitudinal section of the valve element after it is reversed.

FIGS. 20 and 21 show an example of the valve element of the invention that is formed of two or more materials in combination that have different compositions or characteristics. FIG. 20 is a longitudinal section of the deformable portion of the valve element 7 before it is reversed, and FIG. 21 is a longitudinal section of the same deformable portion after the reversal of the valve element 7.

As is clear from FIGS. 20 and 21, the valve element 7 comprises a body portion 78 that provides its skeleton (principal part) and a soft portion 79.

The body portion 78 is made of an elastic material and has a disk-shaped flange 71 on the outer periphery. The valve element 7 is installed and fixed by securing the entire periphery of the flange 71 to the inner surface of the outer needle hub 3 by a suitable method such as fusion or bonding.

The valve element 7 has a deformable portion 73 that undergoes elastic deformation and which is formed inward of the flange 71 (and toward the distal end). The deformable portion 73 provides the soft portion 79 which is made of an elastic material that is softer than the elastic material of which the body portion 78 is made. In the assembled state shown in FIG. 20, the valve element 7 has the soft portion 79 joined or integrated with the outer periphery of the body portion 78. The distal end faces 791 of the soft portion 79 are brought into contact with each other when the deformable portion 73 is reversed (see FIG. 21).

The area of the soft portion 79 near the distal end faces progressively decreases in thickness toward the distal end of the valve element 7. Having this geometry, the deformable portion 73, when reversed, provides closer contact with the inner needle 4 to secure a higher degree of liquid-tightness.

As is clear from FIG. 21, the reversed deformable portion 73 projects toward the basal end. The distal end faces 791 of the soft portion 79 (deformable portion 73) before the reversal now make close contact with each other to close the center hole. As a result, the desired liquid-tightness is secured by the deformable portion 73 both before and after it is reversed. Due to the high flexibility of the soft portion 79 (it expands or shrinks at high ratio), the reversed deformable portion 73 securers adequate liquid-tightness even if the inner needle 4, particularly the hole 72, has a comparatively large outside diameter.

If the soft portion 79 is made of the same material as the body portion 78 (i.e., they are made of materials having the same degree of flexibility), the deformable portion 73 does not have the desired flexibility and when it is reversed, a gap may potentially form near its distal end 77, with the result that the desired liquid-tightness is not provided. There is another problem if the soft portion 79 is made of the same material as the body portion 78 (i.e., they are made of materials having the same degree of flexibility); that is, if the surface of the soft portion 79 at the site corresponding to the distal end faces 791 is roughened or otherwise deteriorated to form small asperities, gaps may potentially result from the asperities when the deformable portion 73 is reversed and this also increases the chance of failure to provide the desired liquid-tightness. In addition, any foreign matter such as tissue fragments that deposits as a result of piercing through the human body will also act as small asperities and may potentially prevent the formation of the desired liquid-tightness.

In the embodiment under consideration, the soft portion 79 is made of a highly flexible material and free from the above-mentioned inconveniences. Particularly in the case where small asperities form in the distal end faces 791 or foreign matter such as tissue fragments deposits in those faces, reversing of the deformable portion 73 allows the ridges (high spots in the asperities) or the foreign matter to enter between the distal end faces 791, thereby preventing the formation of gaps that would otherwise cause leakage of the blood; as a result, even better liquid-tightness is assured.

In the most preferred case of the invention, the deformable portion 73 not yet reversed has a cross section with a noncircular outer peripheral shape (which is square in the embodiment under consideration) as shown in FIGS. 8–11, FIGS. 12 and 13, FIGS. 14 and 15 or FIGS. 16–19 and the valve element 7 has the body portion 78 providing its skeleton (principal part) and the soft portion 79 as shown in FIGS. 20 and 21.

It should be noted that when the deformable portion 73 of the valve element 7 is in a reversed state, the distal ends of the body portion 78 may be in mutual contact or spaced apart.

Thus, in the assembled state with the inner needle 4 passed through the hole 72, the valve element 7 plugs the bore 34 liquid-tightly and prevents the blood from leaking out. Even after the inner needle 4 has been pulled out of the hole 72, the soft part 79 of the reversed deformable portion 73 comes into close contact with the inner needle 4 and plugs the bore 34 liquid-tightly, thereby more effectively preventing the blood from leaking out. If it becomes necessary to break the liquid-tight seal of the bore 34 as in the case of injecting transfusion, one may simply open the hole 72.

The body portion 78 of the valve element 7, particularly its deformable portion 73, may be made of any material that is selected from among various elastic (or soft) materials including, for example, natural rubber, synthetic rubbers such as isoprene rubber, silicone rubber, urethane rubber, styrene-butadiene rubber, fluorinated rubber and acrylic rubber, a porous body of polytetrafluoroethylene, as well as polyamide-, polyester- and otherwise-based thermoplastic elastomers. The soft soft portion 79 may be made of any material that is selected from among various elastic (or soft) materials including, for example, porous bodies of polyurethane, natural rubber, synthetic rubbers such as isoprene rubber, silicone rubber, urethane rubber, styrene-butadiene rubber, fluorinated rubber and acrylic rubber, a porous body of polytetrafluoroethylene, as well as polyamide-, polyester- and otherwise-based thermoplastic elastomers.

The flexibility of the soft portion 79 may typically be represented by the rubber hardness specified under JIS TYPE A. In the embodiment under consideration, the soft portion 79 preferably has a rubber hardness of less than 95, more preferably less than 65.

Preferably, at least one of the body portion 78 and the soft portion 79, in particular, part or all of the soft portion 79 is made of a liquid-tight but gas-permeable material. This offers the advantage that even if no exhaust channel of the type already described above is not provided, gases (e.g. their bubbles) within the bore 34 can be effectively discharged via the valve element 7. This property is possessed by various porous materials including porous bodies of polyurethane and polytetrafluoroethylene. Such porous materials may be rendered water-repellent before they are applied to make the valve element 7.

The method of forming the body portion 78 and the soft portion 79 that have different degrees of flexibility is not limited to any particular type and may be exemplified by i) joining two separate members (the body portion 78 and the soft portion 79) either by fusion or with the aid of an adhesive agent and ii) two-color molding. Alternatively, a heated mold may be pressed against a side of the material of which the soft portion 79 is made, whereupon the area of the soft portion that is being heated under pressure is melted to close the voids, thereby forming the body portion 78 which is harder than the soft portion 79.

In the illustrated embodiment, a clear boundary is shown between the body portion 78 and the soft portion 79. However, the boundary between the two portions need not be clear in the present invention and a gradual change in flexibility may be introduced near the boundary between the body portion 78 and the soft portion 79.

Described below are the steps in a method of using (operating) the self-retaining needle assembly 1 of the present invention.

[1] The outer needle 2 and the inner needle 4 are preliminarily assembled as shown in FIG. 1. When the self-retaining needle assembly 1 is in the assembled state, the valve element 7 has the inner surface 740 (or 74, 741, 742, 743 or 744) of the deformable portion 73 placed in sufficiently close contact with the outer peripheral surface of the inner needle 4 to seal the bore 34 liquid-tightly. In addition, the tip point 41 of the inner needle 4 protrudes beyond the opening 23 at the tip of the outer needle 2 and the flute 46 faces the smaller-diameter portion 21.

Preferably, the step described above has already ended prior to the use of the self-retaining needle assembly 1 (when it is unpacked).

[2] The inner needle 4 and the outer needle 2 in the assembled state is pierced into a blood vessel (a vein or an artery) of the patient. To ensure that degasification of the bore 34 (to be described later) is performed efficiently, the piercing of the two needles is preferably accomplished in such a position that the annular projection 6 faces up in a vertical direction.

When the point tip 41 of the inner needle 4 is pierced into the blood vessel, the blood pressure (the pressure in the blood vessel) causes the blood to flow back through the inner needle 4 toward the basal end until it is introduced into the internal space 51 of the inner needle hub 5, which has sufficient patency to ensure visibility of the "flashback", enabling the surgeon to confirm that the point tip 41 of the inner needle 4 has secured the blood vessel of interest.

As the blood is introduced into the internal space 51, the air in that space passes through the ventilation filter 52 to be discharged to the outside of the inner needle hub 5. This provides a rapid and positive way to confirm the "flashback" of the blood that has flowed into the internal space 51.

[3] As the inner needle 4 and the outer needle 2 are further advanced by a small distance toward the distal end, the tip point of the outer needle 2 is passed into the blood vessel. Then, the blood flows in through the tip opening 23, passes along the flute 46 and flows through the clearance 22 toward the basal end until it is introduced into the bore 34 of the outer needle hub 3. The outer needle 2 and/or the outer needle hub 3 has sufficient patency to ensure visibility of the "flashback", enabling the surgeon to confirm that the distal end of the outer needle 2 has secured the blood vessel of interest.

It should be noted here that as the blood is introduced into the bore 34, the air in said bore passes through the filter 61 in the annular projection 6 providing an exhaust channel, whereupon it is discharged to the outside of the outer needle hub 3. If part or all of the deformable portion 73 of the valve element 7 is made of a liquid-tight but gas-permeable material, the air in the bore 34 is also discharged via the valve element 7. This is also true in the case where the valve element 7 has the soft portion 79 that is made of a more flexible elastic material than its principal portion and which consists of two parts that closely contact each other when the valve element is reversed, provided that the elastic material of which said soft portion 79 is made is liquid-tight but gas-permeable. If this condition is met, the bore 34 can be substantially freed of air at rapid speed of replacement with the blood. As a result, the surgeon can confirm rapidly and appropriately that the outer needle 2 has secured the blood vessel of interest. What is more, any residual air in the bore 34 will not be injected into the blood vessel via the outer needle 2 during the introduction of donor blood (see below) and this presents high procedural safety.

Even if the bore 34 is filled with the blood, the valve element 7 assures liquid-tight seal in the bore (see above) and there is no possibility that the blood overflows the valve element 7 to leak out.

[4] Thereafter, depending on the need, the outer needle 2 is further advanced through the blood vessel until it reaches a predetermined dwelling position.

With the outer needle 2 being held by one hand, the inner needle hub 5 is grabbed by the other hand and pulled toward the distal end so that the inner needle 4 is removed from the outer needle 2. This step causes the self-retaining needle assembly 1 to be in the state shown in FIG. 2. As the inner needle 4 is removed from the outer needle 2, the deformable portion 73 of the valve element 7 is also pulled toward the basal end so that it is reversed according to the mechanism described above.

When the deformable portion 73 is reversed, it is turned inside out and due to its elasticity, the planes (e.g. outer peripheral surfaces and distal end faces) that composed its outer surface before the reversal closely contacted each other to leave no gap in it. Thus, even after the deformable portion 73 was reversed, the valve element 7 assures liquid-tight seal in the bore 34 and prevents the blood from leaking out by overflowing it. If the assembly remains in the assembled state for a prolonged period, time-dependent deterioration and other factors may reduce the elasticity of the deformable portion 73 in areas near its inner surface 740 (or 74, 741, 742, 743 or 744) that has been in close contact with the inner needle 4. According to the invention, the reversed deformable portion 73 is turned inside out and the surface which was outside before the reversal is now positioned inside and shrinks to make a sufficiently close contact with the inner needle 4 that there will be no gap left in the deformable portion 73. As a result, the desired liquid-tightness can be positively secured in the bore 34.

If the valve element 7 has the soft portion 79 that is made of a more flexible elastic material than its principal portion and which consists of two parts that closely contact each other when it is reversed, the deformable portion 73 is turned inside out upon reversal and due to its own elasticity, the distal end faces 791 of the soft portion 79 closely contact each other to close the center hole 72. Thus, even after the reversal of the deformable portion 73, the valve element 7 still provides liquid-tight seal in the bore 34 and prevents the blood from leaking out by overflowing it. If the assembly remains in the assembled state for a prolonged period, time-dependent deterioration and other factors may reduce the elasticity of the body portion 78 in areas near its inner surface that has been in close contact with the inner needle 4. According to the invention, the reversed deformable portion 73 is turned inside out and the surfaces which were outside before the reversal (namely, the distal end faces 791 of the soft portion 78) are now positioned inside and shrink to make a sufficiently close contact with the inner needle 4 that there will be no gap left in the deformable portion 73. As a result, the desired liquid-tightness can be positively secured in the bore 34.

If a reversal assisting means such as the projection 8 is provided, its action already described above allows the deformable portion 73 of the valve element 7 to be reversed more positively.

If part or all of the deformable portion 73 of the valve element 7 is made of a liquid-tight but gas-permeable material, any gas (e.g. bubbles) in the bore 34 can be effectively discharged via the valve element 7 to its basal end. This is also true in the case where the valve element 7 has the soft portion 79 that is made of a more flexible elastic material than its principal portion and which consists of two parts that closely contact each other when the valve element is reversed, provided that the elastic material of which said soft portion 79 is made is liquid-tight but gas-permeable.

[5] As shown in FIG. 3, a blood injecting tool (connector) 9 is fitted into the mating part 33 of the outer needle hub 3 so that a transfusion line is connected to the outer needle hub 3.

During this connecting step, the tip of the blood injecting tool 9 pushes the reversed deformable portion 73 toward the distal end so that the latter makes a second reversal. At the same time, the tip 91 of the blood injecting tool 9 pushes in to enlarge the hole 72 wide enough to permit its passage. As a result, the seal of the bore with the valve element 7 is broken and the interior of the blood injecting tool 9 communicates with the bore 34.

[6] Donor blood is supplied via the transfusion line. As indicated by the arrows in FIG. 3, the blood being send through the tube 94 flows through the blood injecting tool 9 and flows into the bore 34 via the opening 92 at the tip 91 of the tool 9; the blood passes through the bore of the outer needle 2 to be injected into the secured blood vessel of the patient via the tip opening 23 of the outer needle 2.

Any bubbles in the blood will go up as it flows through the bore 34 and they pass through the ventilation filter 61 in the annular projection 6 providing an exhaust channel, whereupon they are discharged to the outside of the assembly. Thus, the annular projection 6 has a capability of degasifying the blood.

If part or all of the deformable portion 73 of the valve element 7 is made of a liquid-tight but gas-permeable material, the bubbles in the bore 34 are also discharged via the valve element 7. This is also true in the case where the valve element 7 has the soft portion 79 that is made of a more flexible elastic material than its principal portion and which consists of two parts that closely contact each other when the valve element is reversed, provided that the elastic material of which said soft portion 79 is made is liquid-tight but gas-permeable. Thus, the blood containing bubbles can be effectively prevented from being injected into the blood vessel and high procedural safety is assured.

[7] When blood injection into the patient ends, the outer needle 2 is removed from the blood vessel of the patient.

While the self-retaining needle assembly of the present invention and the valve element used therewith have been described above with reference to the various embodiments shown in the attached drawings, these are not the sole cases of the invention and the components of the assembly and the valve may be replaced by any functionally equivalent parts.

In the invention, the shape of the valve element 7, particularly its cross-sectional shape (before or after its reversal), the shape of the optional soft portion 79 of the valve element 7 (before or after its reversal) which is made of a more flexible elastic material than its principal portion, provided that said soft portion 79 consists of two parts that closely contact each other when the valve element 7 is reversed, the position of installation of the soft portion 79, its relative volume and other relevant factors are by no means limited to the illustrated examples and may be modified in any appropriate way.

The inner needle 4 is not limited to the illustrated example which is hollow and open at both ends. Its bore may be partly (as at the distal end) closed or, alternatively, it may be of a solid type.

An acicular member such as the inner needle 4 is not the only member that can be passed through the valve element 7 of the invention; it may be replaced by various other members including tubes such as connectors, sheaths and catheters, and rods such as wires.

As described on the foregoing pages, the self-retaining needle assembly of the invention is free from the problem of liquid leakage due to the time-dependent deterioration of the valve element and, therefore, it effectively prevents the blood and other fluids from leaking out to foul the surrounding area or cause other troubles. As a particular advantage, outstanding liquid-tightness is exhibited to prevent the blood or other fluids from leaking out not only before the valve element is reversed (and the outer and inner needles are assembled together) but also before its reversal (with the inner needle removed from the outer needle).

If the cross section of the valve element yet to be reversed has a noncircular outer peripheral shape, the reversing process of the valve element is regular enough to ensure that it can be reversed easily and positively. This advantage is exhibited even if there are variations in the adhesion between the inner surface of the valve element and the outer surface of the inner needle or even if the adhesion changes (drops) due to the time-dependent deterioration of the valve element.

If necessary, the seal created by the valve element may be broken to ensure that the blood and other fluids can be injected easily in a smooth and positive manner.

The valve element has a greater latitude in the selection of materials the valve element can be made of and this allows the valve element to be manufactured easily at a lower cost.

The valve element can be reversed more positively by providing a reversal assisting means.

If the outer needle hub has an exhaust channel, its bore can be rapidly filled with the blood and the securing of the blood vessel of interest by the outer needle can be verified by the "flashback" of the blood.

If part or all of the valve element is made of a liquid-tight but gas-permeable material or if the outer needle hub has an exhaust channel, the degasifying effect (or the ability to remove gases from liquids) prevents the entrance of bubbles into blood vessels or other unwanted areas and thereby ensures high procedural safety. This is also true in the case where the valve element has a soft portion that is made of a more flexible elastic material than its principal portion and which consists of two parts that closely contact each other when the valve element is reversed, provided that the elastic material of which the soft portion is made is liquid-tight but gas-permeable.

The self-retaining needle assembly of the invention has the added advantage of allowing the surgeon to confirm the securing of a blood vessel of interest by the inner and outer needles and this ensures that the needle to be retained in position can be pierced into the blood vessel of interest in an easy and correct way.

What is claimed is:

1. A self-retaining needle assembly comprising:
    a hollow outer needle;
    an outer needle hub that is provided at the basal end of said outer needle and which has a bore communicating with the interior of said outer needle;
    an inner needle to be passed through said outer needle;
    an inner needle hub provided at the basal end of said inner needle; and
    a valve element provided in the bore of said outer needle hub to plug said bore, wherein
    said valve element is a continuous body that is made of an elastic material and which consists of a non-reversible portion and a reversible portion that projects from the non-reversible portion, said non-reversible portion being secured to the inner periphery of said outer needle hub, and said reversible portion has a hole through which said inner needle can be passed.

2. The self-retaining needle assembly according to claim 1, wherein said reversible portion is funnel-shaped.

3. The self-retaining needle assembly according to claim 1, wherein the outer surface of said reversible portion has a noncircular shape in a cross section perpendicular to the direction in which it projects and, when it is reversed, the sides that faced outward before the reversal come into close contact with each other.

4. The self-retaining needle assembly according to claim 3, wherein the outer surface of said reversible portion has a polygonal shape in a cross section perpendicular to the direction in which it projects.

5. The self-retaining needle assembly according to claim 3, wherein the outer surface of said reversible portion has a shape consisting of arcs of a circle combined with straight lines in a cross section perpendicular to the direction in which it projects.

6. The self-retaining needle assembly according to claim 1, wherein said reversible portion comprises thick-walled areas and thin-walled areas in a cross section perpendicular to the direction in which it projects.

7. The self-retaining needle assembly according to claim 1, wherein said reversible portion consists of a principal part and soft parts, said soft parts being made of a more flexible elastic material than the principal part and, when said reversible portion is reversed, coming in close contact with each other.

8. The self-retaining needle assembly according to claim 7, wherein said soft parts contain an area that progressively decreases in thickness from said non-reversible portion to the distal end of the valve element in the direction in which said reversible portion projects.

9. The self-retaining needle assembly according to claim 7, wherein at least said soft parts of said valve element are made of a liquid-tight but gas-permeable material.

10. The self-retaining needle assembly according to claim 1, wherein said inner needle is fitted with a reversal assisting means that assists in reversing said valve element.

11. The self-retaining needle assembly according to claim 1, wherein said valve element is reversed with the aid of the friction that develops when said inner needle is pulled out of said hole.

12. The self-retaining needle assembly according to claim 10, wherein said valve element is reversed with the aid of the action of said reversal assisting means when said inner needle is pulled out of said hole.

13. The self-retaining needle assembly according to claim 1, wherein the outer surface of said reversible portion has a noncircular shape in a cross section perpendicular to the direction in which it projects and, when it is reversed, the sides that faced outward before the reversal come into close contact with each other and wherein said reversible portion comprises thick-walled areas and thin-walled areas in a cross section perpendicular to the direction in which it projects.

14. The self-retaining needle assembly according to claim 13, wherein said reversible portion consists of a principal part and soft parts, said soft parts being made of a more flexible elastic material than the principal part and, when said reversible portion is reversed, coming in close contact with each other.

15. A valve element which is a continuous body consisting of a non-reversible portion and a reversible portion projecting from the non-reversible portion, said reversible portion having a hole through which a tubular or rod member can be passed and being made of an elastic material.

16. The valve element according to claim 15, wherein said reversible portion is funnel-shaped.

17. The valve element according to claim 15, wherein the outer surface of said reversible portion has a noncircular shape in a cross section perpendicular to the direction in which it projects and, when it is reversed, the sides that faced outward before the reversal come into close contact with each other.

18. The valve element according to claim 17, wherein the outer surface of said reversible portion has a polygonal shape in a cross section perpendicular to the direction in which it projects.

19. The valve element according to claim 17, wherein the outer surface of said reversible portion has a shape consisting of arcs of a circle combined with straight lines in a cross section perpendicular to the direction in which it projects.

20. The valve element according to claim 17, wherein said reversible portion comprises thick-walled areas and thin-walled areas in a cross section perpendicular to the direction in which it projects.

21. The valve element according to claim 15, wherein said reversible portion consists of a principal part and soft parts, said soft parts being made of a more flexible elastic material than the principal part and, when said reversible portion is reversed, coming in close contact with each other.

22. The valve element according to claim 21, wherein said soft parts contain an area that progressively decreases in thickness from said non-reversible portion to the distal end of the valve element in the direction in which said reversible portion projects.

23. The valve element according to claim 21, wherein at least said soft parts of said valve element are made of a liquid-tight but gas-permeable material.

24. The valve element according to claim 15, which is reversed with the aid of either the friction that develops when the tubular or rod member is pulled out of said hole or a reversal assisting means that is provided on said tubular or rod member.

25. The valve element according to claim 15, wherein said hole is formed in generally the center of said reversible portion in a cross section perpendicular to the direction in which it projects.

26. The valve element according to claim 15, wherein the outer surface of said reversible portion has a noncircular shape in a cross section perpendicular to the direction in which it projects and, when it is reversed, the sides that faced outward before the reversal come into close contact with each other and wherein said reversible portion comprises thick-walled areas and thin-walled areas in a cross section perpendicular to the direction in which it projects.

27. The valve element according to claim 26, wherein said reversible portion consists of a principal part and soft parts, said soft parts being made of a more flexible elastic material than the principal part and, when said reversible portion is reversed, coming in close contact with each other.

\* \* \* \* \*